United States Patent [19]

Haindl

[11] Patent Number: 5,423,776
[45] Date of Patent: Jun. 13, 1995

[54] FLEXIBLE COUPLING, IN PARTICULAR FOR COUPLING A FLEXIBLE CATHETER TO A PORT OF A PORT CATHETER SYSTEM

[76] Inventor: Hans Haindl, Hauptstr.39, 30974 Wennigsen, Germany

[21] Appl. No.: 204,224

[22] PCT Filed: Sep. 4, 1992

[86] PCT No.: PCT/EP92/02038
§ 371 Date: Mar. 3, 1994
§ 102(e) Date: Mar. 3, 1994

[87] PCT Pub. No.: WO93/04733
PCT Pub. Date: Mar. 18, 1993

[30] Foreign Application Priority Data

Sep. 7, 1991 [DE] Germany .................. 41 29 781.4

[51] Int. Cl.[6] ............................................. A61M 25/00
[52] U.S. Cl. ...................................... 604/283; 604/905
[58] Field of Search ............... 604/283, 280, 905, 264; 285/248, 177, 259

[56] References Cited

U.S. PATENT DOCUMENTS 1,361,758 12/1920 Ewald ............................ 285/248

FOREIGN PATENT DOCUMENTS 343910 11/1989 European Pat. Off. .
2385969 10/1978 France .
2628639 9/1989 France .

Primary Examiner—John D. Yasko
Attorney, Agent, or Firm—Allegretti & Witcoff, Ltd.

[57] ABSTRACT

Coupling for connecting an implantable port catheter to flexible catheter tubes of varying size and diameter. A rigid tapered tube extends from a port opening in the catheter system housing and the catheter tube slides onto the end of the rigid tube. A clamping sleeve having a bore larger than the outer diameter of the tube has a circular gripping shoulder which bites into the flexible tube as the tube and sleeve are pushed onto the tapered surface of the rigid tube extending from the port opening to clamp the flexible catheter tube firmly between the shoulder and the tapered surface. The distance between the gripping shoulder and the tapered tube is variable to accommodate the size of the flexible catheter tube.

3 Claims, 1 Drawing Sheet

FLEXIBLE COUPLING, IN PARTICULAR FOR COUPLING A FLEXIBLE CATHETER TO A PORT OF A PORT CATHETER SYSTEM

The invention concerns a flexible coupling for connecting a flexible catheter to a port of a port catheter system. This application is A 371 of PCT/EP92/02038, filed Sep. 4, 1992.

BACKGROUND OF THE INVENTION

In a known catheter system the port consists of a flat housing containing a chamber which is covered by a covering consisting of silicon and penetrable by a cannula. A flexible catheter can be connected to the chamber. Port catheters are implanted so that the hose can be led to the application site, e.g., a vessel. To bring a medication to the application site, the skin and the silicon covering are pierced with a cannula and the medication injected into the chamber, from where, through the coupled catheter, it reaches the application site where it is used.

The implantation of a port catheter system is considerably facilitated if the port and the flexible catheter are disconnectably connected to each other, so that both parts can be handled individually for the implantation. It is especially useful if no special coupling part is necessary on the flexible catheter, so that the latter can be cut off as required and thus be coupled in any desired length to the port. Known flexible catheters provide tubular parts for sliding on the flexible catheter as well as clamping couplings or snap-action squeezing couplers of various designs for the coupling of the flexible catheter. Common to all these known forms of execution is that in each instance they are suitable for a given hose material, a given hose diameter and a given wall thickness of the hose. For this reason, it is necessary to have available a large number of different flexible catheter coupling types for different hose diameters, wall thickness and kinds of material.

SUMMARY OF THE INVENTION

The object of the invention is to create a flexible coupling of the type in question which is suitable for the coupling of a flexible catheter of varying diameter, varying wall thickness and varying material to a port of a port catheter system.

The invention consists in tapering the tubular part over which the hose or catheter tube slides so that the hose is enlarged with increased engagement. Correspondingly, there results an expanding contact area on the outer surface of the hose. This contact area is operable for hoses of different diameters. According to another important characteristic of the invention, a clamping sleeve is provided which can be slid over the hose and locked to the housing of the port catheter system. The sleeve has an internal squeezing or gripping edge or shoulder whose internal diameter is smaller than the largest expanded diameter of the hose when pushed onto the tapered tubular part. When the clamping sleeve and hose is pushed onto the tubular part, the gripping edge comes in contact with the exterior surface of the hose at a given point, squeezes it somewhat and pushes the hose a little farther onto the tubular part as the sleeve is locked to the housing. In this way, a very positive connection is provided between the clamping sleeve and the hose end which assures a secure mounting of the end of the hose on the tubular part. Due to the high pressure in the area of the squeezing edge, a good seal also is made with the tubular part. In the secured position then the clamping sleeve is connected with the housing on which the tubular part is located, so that a total coupling is produced.

Since the catheter hose or tube to be coupled is slid completely onto the tapered tubular part and is thus enlarged to provide a secure connection, hoses of very different diameters and also of different wall thicknesses or material composition can be securely coupled. It is not necessary that clamping sleeve be designed differently in each case. If a complete mounting of a small diameter hose on the tubular part is not possible, then it is necessary that the squeezing edge must have a correspondingly different position with respect to the tubular part in order to compress the hose. The internal width or diameter of the squeezing edge must be smaller than the external diameter of the hose which is only partially mounted on the tubular part at the site of the squeezing edge. In such a case, it can therefore be necessary that for different hose diameters clamping sleeves with different positions of the squeezing edge or different internal widths of the squeezing edge be kept available. This is, however, not a particular drawback, since the clamping sleeves are very cheap small parts and available in different dimensions.

The means for locking the clamping sleeve to the housing can be designed basically in any way desired. It is advantageous, however, to make them screw-on, bayonet, or snap-on couplings. The coupling can thus be accomplished quickly and simply.

Another feature of the invention is that the clamping sleeve when connected with the housing extends beyond the terminal or free end of the tubular part. This protects mechanically the end of the tubular part, which is of special importance when this end is very thin.

The flexible coupling of the invention is quite generally suitable for the coupling of a hose to a tubular part, but it is particularly useful with flexible catheters because here it provides to a special degree a secure, simple and lasting connection.

DETAILED DESCRIPTION

Figure 1:
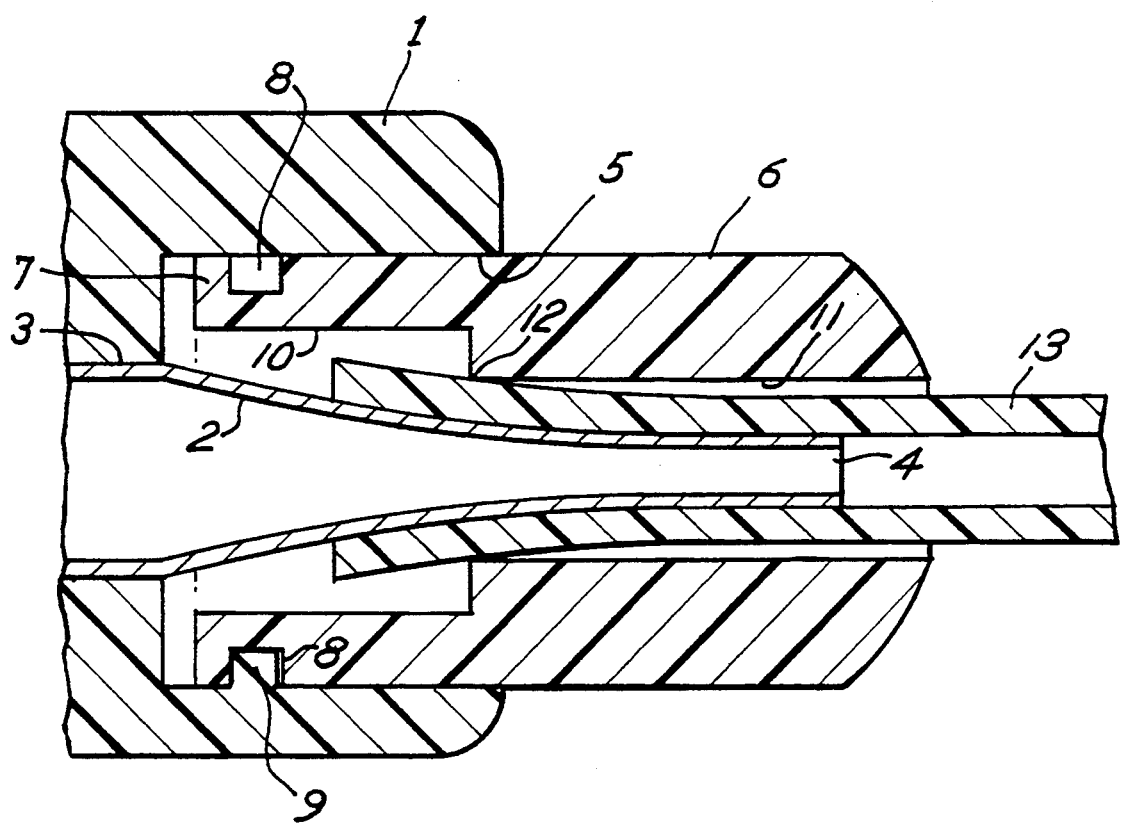

The single FIGURE in the drawing shows in section and partly cut away a coupling constructed in accordance with the invention connected to the housing of a catheter system through a port.

The flexible coupling connects to a housing 1 having a tubular part 2 extending from a port 3 in the housing 1. The tubular port 2 is preferably cemented in or swaged into the housing. The housing 1 and tubular part 2 may be formed in one piece, which is especially advantageous when the two are made of plastic. The rigid tube 2 may be made of steel. The tube 2 has a base at the port opening 3 and tapers trumpet-like toward its small end 4.

The housing 1 has a cylindrical recess 5, concentric with the tubular part 2, into which a clamping sleeve 6 is inserted. The inserted end 7 of sleeve 6 has recesses 8 which in the top view (not shown in the drawing) are L-shaped in the manner of a bayonet lock and together with projections 9 on the housing 1 constitute a bayonet lock.

The clamping sleeve 6 has internal walls 10 and 11 of differing diameters between which a gripping shoulder or edge 12 is formed whose inside diameter corresponds to the inside diameter of the inner wall 11. Edge 12 is located with respect to tapered tube 2 where, due to its connection position through the bayonet connection 8, 9, the edge has a smaller inside diameter than the outside diameter of a hose 13 mounted on the tube 2. The inside diameter of the gripping edge 12 and its spacing from the bayonet connection 8, 9 is such that in the connected state the gripping edge 12 has squeezed the hose 13 against the wall of tapered tube 2 and holds it fast.

In assembling the flexible coupling, the separate clamping sleeve 6 is pushed over and beyond the end of the hose 13. The hose end is pushed onto the free end 4 of the conically expanding tube 2 as far as possible, but in any case so far that the outside diameter of the expanding end of the hose 13 is larger than the inside diameter of the gripping shoulder 12. Then the clamping sleeve 6 is pushed toward the housing 1 and moved into the recess 5 whereupon the edge 12 digs into the outer surface of the hose 13 until finally the bayonet connection 8, 9 is in locked position. In this position, the gripping edge 12 is buried solidly in the outer surface of the hose 13 and holds it firmly against any withdrawal from the tube 2. Also, by means of the gripping edge 12, the hose 13 is pressed firmly against the outside wall of the tube 2 so that a tight and permanent connection is achieved.

I claim:

1. A tube coupling for detachably connecting a flexible catheter tube to a port catheter system comprising
   a housing containing a port opening,
   a rigid tube extending from said port opening, having a base at the port opening and an external tapered surface which decreases in diameter in a direction away from said base to the terminus of the tube,
   a flexible catheter tube having an internal diameter equal to or greater than the diameter of said tapered rigid tube at said terminus,
   a clamping sleeve having an internal bore with a diameter greater than the external diameter of said flexible catheter tube,
   a circular gripping shoulder on the circumference of said bore, said shoulder having a diameter smaller than said rigid tube at its base, and
   means for locking said clamping sleeve to said housing and simultaneously gripping said flexible catheter tube,
   whereby when said sleeve and a flexible catheter tube therein is pushed onto said tapered surface during the locking operation, the distance between said gripping shoulder and said tapered surface gradually decreases causing said flexible catheter tube to be clamped firmly between said shoulder and the external tapered surface of said rigid tube.

2. The tube coupling of claim 1 in which said locking means is a bayonet connector.

3. The tube coupling of claim 1 in which said clamping sleeve, in locked position, extends beyond said terminus of said rigid tube to protect it from breakage.

* * * * *